United States Patent [19]

Baurmeister et al.

[11] Patent Number: 4,828,587
[45] Date of Patent: May 9, 1989

[54] DEVICE FOR SEPARATING GAS BUBBLES FROM FLUIDS

[75] Inventors: Ulrich Baurmeister; Michael Pelger, both of Wuppertal, Fed. Rep. of Germany

[73] Assignee: Akzo NV, Netherlands

[21] Appl. No.: 75,726

[22] Filed: Jul. 20, 1987

[30] Foreign Application Priority Data

Jul. 18, 1986 [DE] Fed. Rep. of Germany ....... 3624363

[51] Int. Cl.⁴ .............................................. B01D 19/00
[52] U.S. Cl. ..................................... 55/159; 210/188; 210/436; 604/126
[58] Field of Search .................. 55/159, 321; 604/126, 604/406; 210/188, 456

[56] References Cited

U.S. PATENT DOCUMENTS

| | | | |
|---|---|---|---|
| 3,523,408 | 8/1970 | Rosenberg | 55/159 |
| 3,778,971 | 12/1973 | Granger et al. | 55/159 |
| 3,854,907 | 12/1974 | Rising | 55/159 |
| 4,276,170 | 6/1981 | Vaillancourt | 55/159 X |
| 4,278,084 | 7/1981 | Pope | 55/159 X |
| 4,336,036 | 6/1982 | Leeker et al. | 55/159 |
| 4,531,954 | 7/1985 | Klein | 55/159 |
| 4,568,366 | 2/1986 | Frederick et al. | 55/159 |
| 4,615,694 | 10/1986 | Raines | 604/126 |
| 4,636,307 | 1/1987 | Inoue et al. | 210/188 |

FOREIGN PATENT DOCUMENTS

| | | |
|---|---|---|
| 2458405 | 6/1975 | Fed. Rep. of Germany . |
| 2604003 | 8/1977 | Fed. Rep. of Germany . |
| 2317750 | 9/1977 | Fed. Rep. of Germany . |
| 2851838 | 5/1979 | Fed. Rep. of Germany . |
| 1959679 | 7/1979 | Fed. Rep. of Germany . |
| 3011681 | 10/1980 | Fed. Rep. of Germany . |
| 3039557 | 7/1982 | Fed. Rep. of Germany . |
| 3143456 | 5/1983 | Fed. Rep. of Germany . |
| 2737745 | 3/1984 | Fed. Rep. of Germany . |
| 3304951 | 8/1984 | Fed. Rep. of Germany . |
| 85/00986 | 3/1985 | PCT Int'l Appl. . |
| 85/00987 | 3/1985 | PCT Int'l Appl. . |
| 565578 | 8/1975 | Switzerland . |
| 1221625 | 2/1971 | United Kingdom . |

Primary Examiner—Charles Hart
Attorney, Agent, or Firm—Oliff & Berridge

[57] ABSTRACT

A device for separating gas bubbles from infusion fluids or human-body fluids by means of fluid-repellent, gas-permeable, microporous degassing elements with a casing, which has an inlet opening for the fluid to be degassed, an outlet opening for the degassed fluid, and at least one outlet opening for gas. The degassing element is disposed at least in the area of the casing in which gas bubbles occur, wherein the degassing element comprises at least one degassing capillary whose inner cavity is closed against the passage of fluid, and an outlet opening for the gas. Preferably, this device is used as an infusion filter, in which case a wettable, gas-impermeable microporous filter is additionally disposed in the casing. The wettable, gas-impermeable microporous filter may comprise filter capillaries, in which case the filter capillaries and the degassing capillaries can be disposed in such a way that they have only one common embedment.

16 Claims, 5 Drawing Sheets

DEVICE FOR SEPARATING GAS BUBBLES FROM FLUIDS

TECHNICAL FIELD

The invention relates to a device for separating gas bubbles from infusion fluids or human-body fluids by means of fluid-repellent, gas-permeable, microporous degassing elements with a casing. The casing is provided with an inlet opening for the fluid to be degassed, an outlet opening for the degassed fluid, and at least one outlet opening for gas. The degassing element is disposed at least in the area of the casing in which gas bubbles occur.

BACKGROUND OF THE INVENTION

This type of device is known in more than one publication of prior art (see, e.g., West German Laid-Open Application No. 1,959,679, West German Patent Specification No. 2,317,750, West German Laid-Open Patent Application No. 3,304,951). In the devices of known construction, the degassing element is a flat membrane (West German Patent Specification No. 2,317,750) or at least part of the casing (West German Laid-open Patent Application No. 3,304,951). As a rule, these devices are attached to the arm of the patient, as a result of which the casing, though it can no longer be rotated about the longitudinal axis, can be brought into an inclined position by the arm movement of the patient. In this respect, viewed in the longitudinal direction of the casing, the degassing element must be disposed at both ends of, and in the area of or above, the longitudinal axis of the casing so as to produce a reliable separation of the gas bubbles from the fluid in any inclined position of the casing. All the devices of known construction have the disadvantage that, owing to the required porosity of the degassing elements, the latter are not transparent, and it is therefore impossible to check whether the gas bubbles are being removed from the fluid. Moreover, when using flat membranes as the degassing element, extra work is necessary to tightly embed the degassing elements during manufacture, which results in greater expense for the known devices. This has particularly unfavorable consequences, since these devices are disposable articles and are therefore mass-produced. Since these devices are usually attached with adhesive plaster to the patient's arm, the danger exists that the outlet opening for the gas, frequently formed as an opening in the casing wall facing away from the patient's arm, will be covered by the adhesive plaster, thereby preventing effective degassing of the fluid.

SUMMARY OF THE INVENTION

An object of the present invention is to provide a device for separating gas bubbles from fluids, in which the existence of gas bubbles can be observed and the effectiveness of the degassing can be monitored. Furthermore, the subject device is designed in such a way that it can be manufactured inexpensively. In particular, the effectiveness of the degassing element is ensured in very simple fashion even in an inclined position, or even in a vertical position of the longitudinal axis of the casing. The effectiveness of the degassing element is ensured even if adhesive plaster is unfavorably applied.

These and other objects of the invention are achieved by making the degassing element of at least one capillary comprising an inside cavity closed against the passage of fluid, and an outlet opening for the gas. The casing can be made of transparent material, so that the capillary (capillaries), whose wall consists of a fluid-repellent, gas-permeable, microporous material, and the existence of gas bubbles can be readily observed. The position and length of the degassing capillary (capillaries) is (are) chosen such that the degassing function is ensured, i.e., the degassing capillary (capillaries) is (are) disposed at least in the part of the casing in which gas bubbles occur.

BRIEF DESCRIPTION OF THE DRAWINGS

The invention will now be discussed in greater detail in conjunction with the accompanying Figures, in which.

DETAILED DESCRIPTION OF PREFERRED EMBODIMENTS OF THE INVENTION

Figure 1:
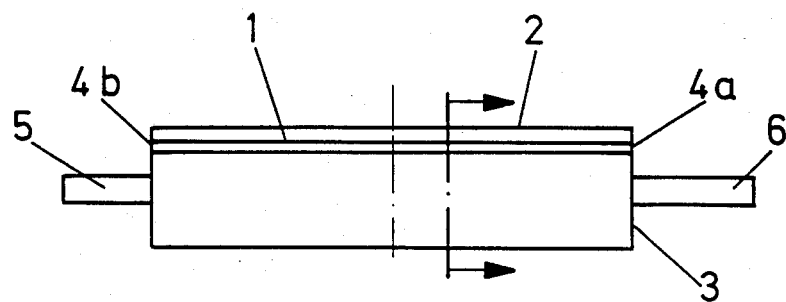
FIG. 1 is a longitudinal section of a degassing device.

In the simplest case, the degassing capillary may extend over the entire, or almost the entire, length of the casing, whereby in each case preferably at least one end of the capillary (capillaries) disposed in the axial direction of the casing is used as the outlet opening for the gas. Needless to say, either both ends of the degassing capillaries are outlet openings or the end not used as the outlet opening is closed against the passage of fluid.

Suitable materials for the fluid-repellent, gas-permeable, microporous degassing capillaries are, for example, polypropylene, polyvinylidene fluoride or polytetrafluoroethylene. The manufacture of such degassing capillaries can be carried out, for example, in the manner described in West German Laid-open Patent Application No. 3,049,557 or West German Laid-open Patent Application No. 2,737,745. A particularly advantageous embodiment of the device according to the invention results if, during rotation about its longitudinal axis in any (swivelling) position, it performs a good degassing job. This is achieved by the device of the invention by distributing a plurality of degassing capillaries along the circumference on the inner face of the casing jacket. The same function can alternatively, or additionally, be achieved if the degassing capillaries are disposed in such a way that they extend from one casing wall to the opposite casing wall, so that the degassing capillaries form with each other a net-like structure which, at least in part, is disposed perpendicularly to the direction of flow of the fluid to be degassed. For this purpose, the degassing capillaries can be interlaced with each other.

By appropriate adjustment of the openings of the net-like structure, it can be ensured that even the smallest air bubbles reach with certainty a degassing capillary even over a short distance in the direction of flow.

Such advantages are also achieved if a plurality of degassing capillaries parallel to each other is used in the form of a small band. These capillaries can be disposed either in the direction of flow or perpendicular thereto. The small band may also have a tubular shape, which at one end, for example, is closed in the manner of a thimble.

The shape of a small band or of a net-like structure can be simply achieved by disposing the degassing capillaries as weft and/or warp threads of a woven fabric. If only the weft, or only the warp, threads are degassing capillaries, yarns or threads which need only be compatible with the fluid to be degassed are used for the other type of thread (warp or weft threads). As a rule, threads of synthetic polymers are used for this purpose.

A wettable, gas-impermeable, microporous filter may additionally be contained in the device of the invention. Such a filter subdivides the casing into a first compartment with the inlet opening and a second compartment with the outlet opening, the degassing capillary or capillaries in the space between filter and casing wall being disposed at least above the filter. (Whenever reference is made herein that the degassing capillary is disposed above the filter, this means that the degassing capillary is placed above the filter in the casing when in the operating position.)

Filters which are suitable for the filtration of the fluid and which may also be membranes, can inherently have, or can have by means of a special treatment, the property of being wettable (for example, lyophilic or hydrophilic) by the fluid to be filtered. Analogously, the same is true for the fluid-repellent (e.g., lyophobic or hydrophobic) gas-permeable material for the degassing capillary.

Suitable materials of the filter membrane include, for example, polyamide-6,6, polyamide-6, cellulose, cellulose acetate and polyvinyl acetate (PVA). Suitable materials for the fluid-repellent gas-permeable microporous parts of the device according to the invention include, for example, polypropylene, polyvinylidene fluoride or polytetrafluoroethylene.

The average pore size for the filter is directed towards the particular filtering effect desired and is, for example, 0.2 micron for sterile filtration or 1 micron for particle filtration. The maximum pore size of the wettable, gas-impermeable microporous filter (membrane) must be such that the associated bubble pressure (i.e., the pressure at which gas penetrates through the filter layer by displacing the fluid from the pores) is higher than the filtration pressure. The bubble pressure, and thereby the filtration pressure that can be applied, increases as the size of the largest pore of the wettable microporous filter layer decreases.

On the other hand, the pore size of the fluid-repellent, gas-permeable, microporous degassing capillary must be chosen such that the filtration pressure is lower than the pressure needed for fluid intrusion. The pressure for fluid intrusion, also known as the fluid-penetration pressure, increases as the maximum pore size of the degassing capillary decreases and as the difference of the surface tensions of fluid and the fluid-repellent gas-permeable microporous material increases.

These relationships existing for the interaction of fluids and gases with microporous materials are to be considered when designing and using the device incorporating the invention.

The separation of gases from fluids by means of microporous, fluid-repellent materials is no problem if fluids with a high surface tension are involved, such as water.

A reduction in the difference of the surface tension of fluid and material (e.g., in the presence of additives which lower the surface tension) can be compensated for by reducing the pore size of the material, or by choosing a material with a suitable pore size. Where appropriate, the surface available for degassing must be increased. Moreover, the fluid-repellent property of a material can also be deleteriously affected or entirely lost at high fluid temperatures. This means that, for the porous parts of the device according to the invention which cause the gases to be separated from the fluid, it is necessary to choose a material with which the escape of fluid is prevented under specified operating conditions. By a simple preliminary test, one can ascertain whether the fluid-repellent property present in a porous material under normal conditions is still present under operating conditions as well.

The device embodying the invention is also suitable if, for its intended use, there is an appreciable over-pressure relative to the ambient pressure in the fluid, as may be the case, for example, with infusion filters with an upstream pump. The outlet openings of the degassing capillaries may also be combined into a single outlet opening, so that a reduced pressure can be applied to the inner cavity of the degassing capillaries to increase their effectiveness.

It is of particular advantage if the filter has at least one filter capillary and the inner cavity of the filter capillaries, at least in part, forms the second compartment. Compared with flat filters, a particularly large effective filter surface is obtained by means of filter capillaries.

The degassing of the fluid can be carried out with great success if the degassing capillary (capillaries) is (are) wound several times loosely around the filter capillary (capillaries) along the length thereof.

It is also possible that, with the device incorporating the invention, the filter capillaries are disposed in the form of a bundle, along whose circumference the degassing capillaries are disposed.

Especially if the inside cavities of the degassing capillaries are in contact with the surrounding atmosphere in the area of the inlet opening of the fluid to be vented off, the degassing capillaries and filter setup can lie beside each other in any desired arrangement. In particular, every filter capillary can be disposed next to a degassing capillary, and every degassing capillary next to a filter capillary.

In those embodiments in which filter capillaries and degassing capillaries are to be disposed beside each other, it has proved best to combine the filter capillaries and the degassing capillaries as weft and/or warp threads into one woven fabric or several woven fabrics. If only the weft threads or only the warp threads are capillaries, the yarns or threads, which preferably consist of synthetic polymers, but which must be compatible with the fluids to be degassed, are used for the other (warp or weft) threads.

Especially advantageous is a device in which the filter capillaries and degassing capillaries are disposed in a tubular casing in the form of an extended U. In this embodiment, all ends of the capillaries are embedded in a sealing compound at one end of the casing in such a way that there terminate in the central area of the embedment point only filter capillaries and in the outer area thereof only degassing capillaries. The end of the casing provided with the sealing compound is shut off by a downstream cap containing the outlet opening for the degassed fluid in such a way that the ends of the filter capillaries terminate inside, and the ends of the degassing capillaries terminate outside, the downstream cap.

When reference is made herein to the fact that that the ends of the capillaries are embedded in a sealing compound, this means that the sealing compound tightly surrounds the individual capillaries, but the inside cavities of the capillaries are not closed by the sealing compound.

In this case, it has proved expedient for the ends of the degassing capillaries in the area of the sealing compound to be disposed at least substantially axially parallel to the casing.

Here, it has proved particularly advantageous for the cavities of the degassing capillaries to be in communication with a circumferential channel formed by the downstream cap of the sealing compound and the casing. With this embodiment it is made certain that, even if relatively large parts of the groove are covered by adhesive plaster, degassing will occur.

In order to ensure good sealing between cap and sealing compound as the point of separation between the ends of the filter capillaries and of the degassing capillaries, a ring between cap end and sealing compound has proved the most satisfactory expedient. This ring may be tapered toward the sealing compound, so that it penetrates in part into the sealing compound when the downstream cap is put in place. However, the ring can also be inserted prior to introduction of the sealing compound and embedded therein. It may be bonded to the casing and/or to the downstream cap, e.g., by cementing, so that the downstream cap is bonded to the casing, for example, via the ring. This ring does not absolutely have to be circular. Polygons or elliptical rings can also be used.

Materials commonly used for the embedment of capillaries, which may be thermoplastic or self-curing, can be used for the sealing compound.

Casings with practically all possible cross sections, especially with an elliptical, triangular or circular cross section, may be used as tubular casings.

Figure 2:
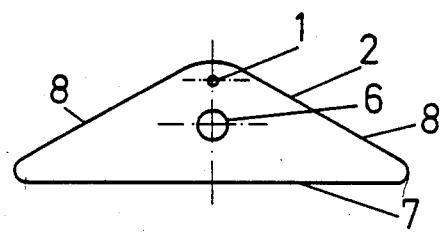
FIG. 2 is a cross-sectional view of the degassing device shown in FIG. 1.

In a particularly simple degassing device, as shown, for instance, in FIGS. 1 and 2, the degassing capillary 1 is disposed in the upper area of the casing 2. The casing 2 has, in cross section, a triangular outline, one side 7 of the triangular outline being much longer than the two other sides 8, so that only the side 7 can be used for placement on the patient's arm. For optimum placement of the device according to the invention on the patient's arm, the side 7 is curved slightly inward. Thus, it is ensured that the degassing capillary 1 in the embodiment shown extends with certainty into the upper area of the degassing device, so that the gas bubbles rising during the flow through the casing 2 come into contact with the degassing capillary 1 and are evacuated through the microporous layer into the inner cavity of the degassing capillary 1. The two ends of the degassing capillary 1 are each embedded into the end walls 3 of the casing 2 in such a way that the inner cavity is in communication with the surrounding atmosphere. Thus, the inner cavity of the degassing capillary 1 forms two outlet openings 4a and 4b for the gas. There are provided on the casing one inlet opening 5 for the fluid to be degassed and one outlet opening 6 for the degassed fluid.

If, in a casing with a triangular cross section, all three sides of this triangle were to have the same length, at least one degassing capillary would have to be located in each corner of this triangular cross section in order to ensure effective degassing in any position.

Figure 3:
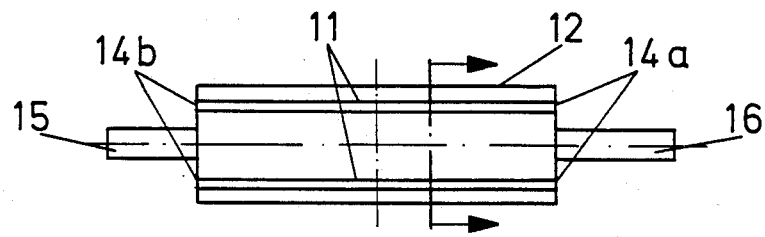
FIG. 3 is a longitudinal section of another degassing device.
Figure 4:
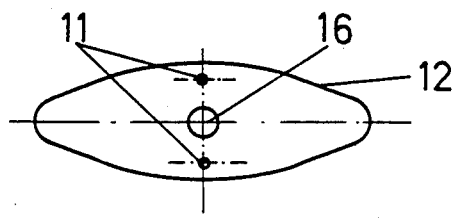
FIG. 4 is a cross section of the degassing device shown in FIG. 3.

The casing 12 of the degassing device illustrated in FIGS. 3 and 4 has an oval cross section. In order to ensure that basically one degassing capillary is disposed in the upper area, even though the device shown can be attached to the patient's arm in two positions rotated 180° relative to each other, two degassing capillaries 11 are provided in this device. The ends of both degassing capillaries are again embedded into the end faces, each degassing capillary having two outlet openings 14a, 14b for the gas. Again, the casing 12 has an inlet opening 15 for the fluid to be degassed and an outlet opening 16 for the degassed fluid.

Figure 5:
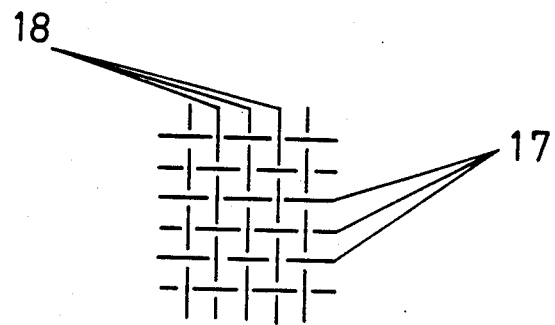
FIG. 5 shows a woven fabric in which warp and weft threads comprise capillaries.
Figure 6:
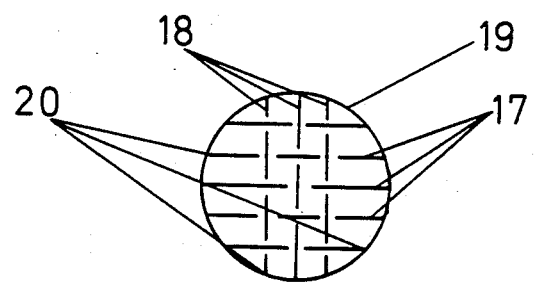
FIG. 6 is a cross section of a degassing device with an embedded woven fabric according to FIG. 5.

FIG. 5 shows schematically a woven fabric in which both the weft threads 17 and the warp threads 18 comprise degassing capillaries. As shown in FIG. 6, such a woven fabric can be embedded between two casing parts 19, so that a close-meshed net is formed by the degassing capillaries to trap gas bubbles with certainty. Again, the degassing capillaries have outlet openings 20 for the gas.

Figure 7:
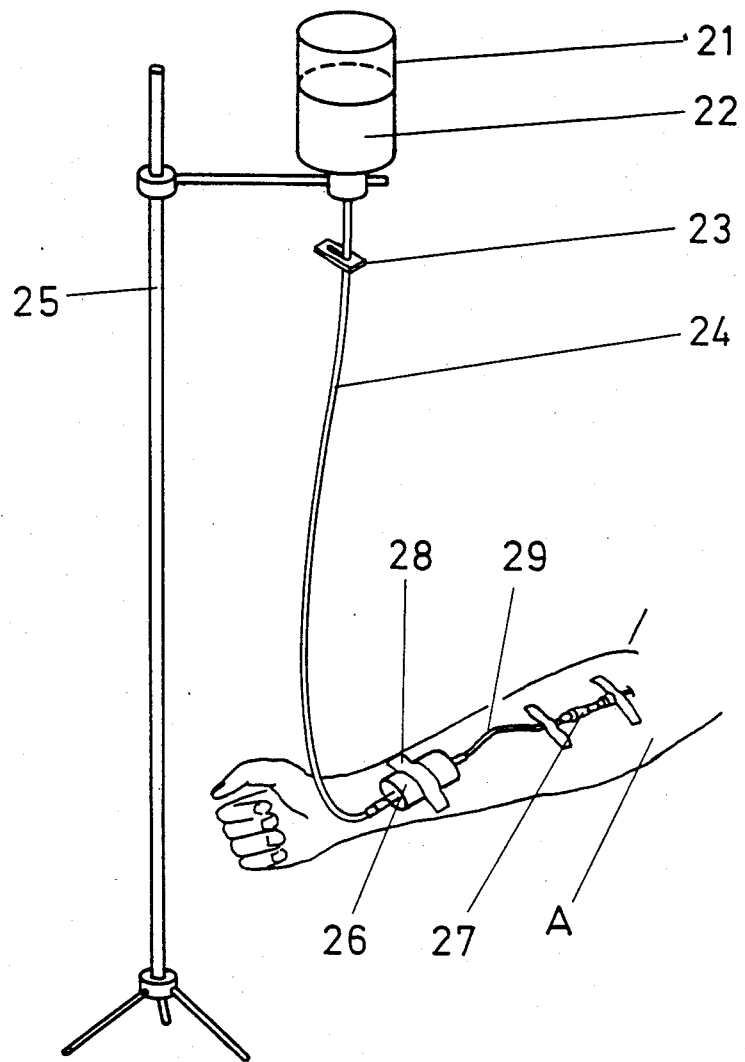
FIG. 7 is a diagram showing one application of the devices taught by the invention.

FIG. 7 shows one application of a device 26 according to the invention. From the supply cylinder 21, which is positioned on a stand 25, an infusion fluid 22 is passed through a hose 24 to a device 26 for separating gas bubbles and filtering this infusion fluid. This degassing and filtering device is pasted onto the forearm A of a patient by means of an adhesive plaster 28. The feed rate of the infusion fluid can be controlled by the dosing aid 23. From the degassing and filtering device 26, the infusion fluid passes through another hose 29 and an infusion needle 27 into the bloodstream.

Figure 8:
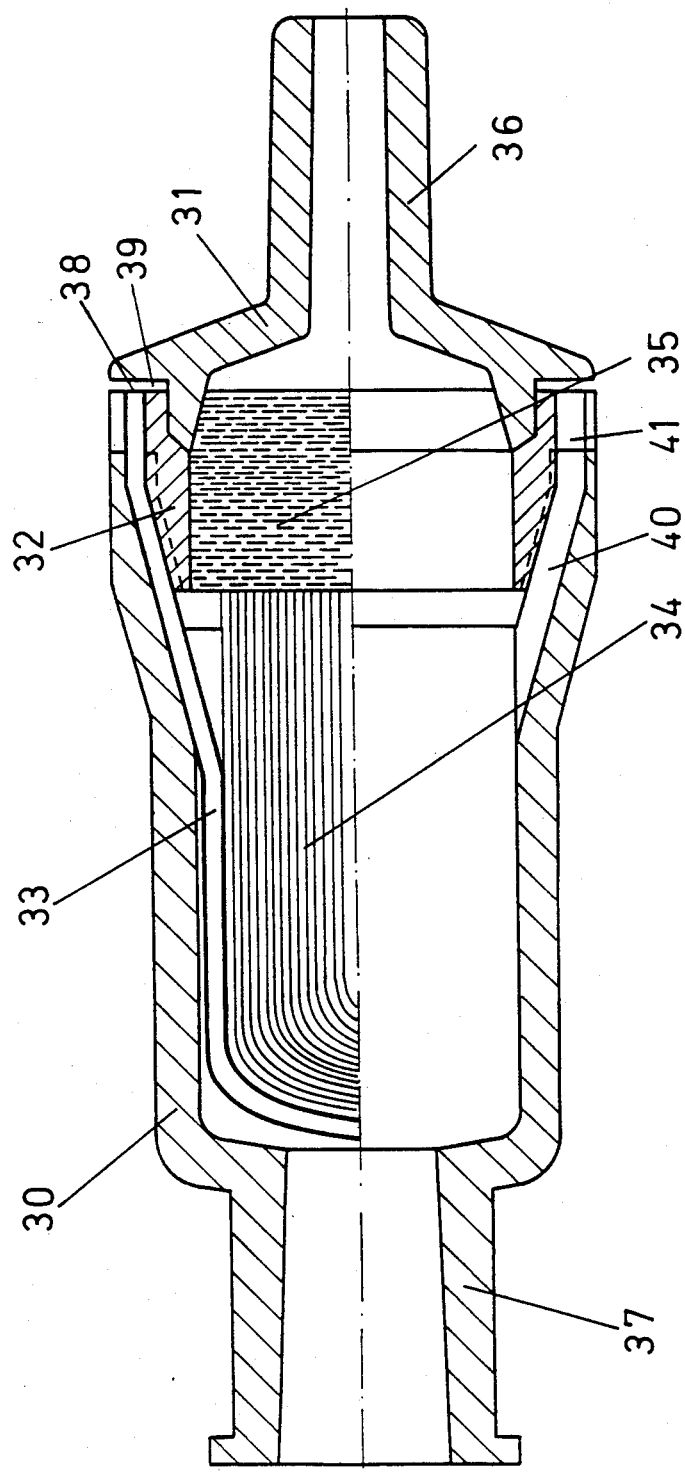
FIG. 8 is a longitudinal section of an embodiment of a degassing and filtering device according to the invention.

A degassing and filtering device according to the invention suitable for such an application is shown in Figure 8. A tubular casing 30 with an inlet connection 37 for the fluid to be degassed is closed via a ring 32 by a downstream cap 31 with an outlet connection 36. In the casing 30 there are cut at least two grooves 40, in pairs and in diametrically opposed positions, into which are embedded, with sealing compound, the degassing capillaries 33 disposed in the form of a U in the casing 30, the two ends of the U being inserted into two diametrically opposed grooves. The ring 32 inserted into the casing closes off the grooves 40, so that the ends of the degassing capillaries 33 are tightly embedded in the area of the ring 32. Furthermore, the ring 32 has grooves or bores 41 in the outer rim, into which the ends of the degassing capillary are extended further, or which serve as an extension of the inside cavities of the degassing capillaries 33. The downstream cap 31 connected to the casing in a manner not shown herein (e.g., by means of snap locks) is supported on the interior of the ring 32. The downstream cap 31 may also be connected to the ring 32 and/or the ring 32 may be connected to the casing 30, e.g., by ultrasonic welding. The ring 32 serves at the same time to receive the sealing compound 35, into which are embedded filter capillaries 34, which are also introduced in the form of a U into the casing 30. In the area of the casing 30, the filter capillaries 34 are surrounded by the degassing capillaries 33, so that the gas bubbles filtered off by the filter capillaries 34 can escape through the degassing capillaries 33 in any tilted position of the axis. If the degassing capillaries 33 are uniformly distributed along the inner circumference of the casing 30, the latter may have a circular-cylindrical cross section, because now rotation about the axis of the casing 30 is no longer of importance for venting off the degassing capillaries. The ends 38 of the degassing capillaries 33 terminate in a circumferential groove 39 formed by the ring 32 and the downstream cap 31. Since during positioning, with adhesive plaster, of the degassing and filtering device illustrated in FIG. 8, even if the adhesive plaster is placed in the area of the groove, at least part of the groove is not pasted over by the adhesive plaster (e.g., in the area between the degassing and filtering device and the patient's arm), the degassing operation is basically ensured.

Figure 9:
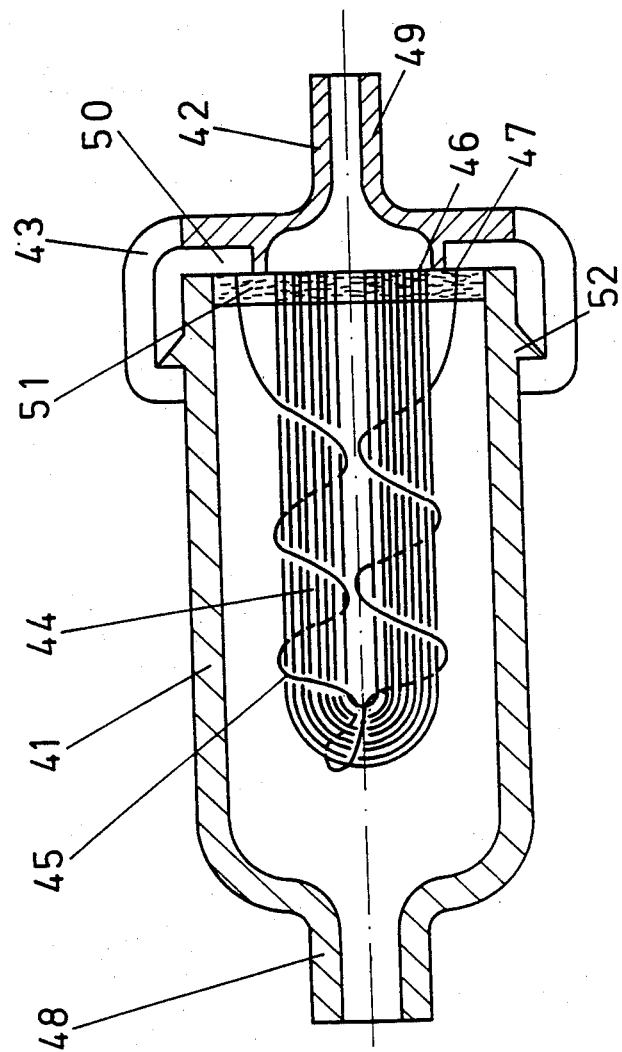
FIG. 9 is a longitudinal section of another embodiment of a degassing and filtering device according to the invention.

FIG. 9 shows another advantageous embodiment of a degassing and filtering device according to the invention. A filter-capillary bundle 44, which is inserted in the form of a U into the casing 41, is wound helically within the casing 41 by a degassing capillary 45. In the central area are embedded into a sealing compound 51 the ends 46 of the filter capillaries 44, and along the outer circumference are embedded the ends 47 of the degassing capillaries 45, with the cavities of both capillary types remaining open to the outside. A downstream cap 42 is formed in such a way that it subdivides the sealing compound into two areas. The central area, in which the ends 46 of the filter capillaries 44 terminate, runs into the outlet connection 49 of the downstream cap 42. The outer area comprises a circumferential groove, which is formed by the downstream cap 42, the sealing compound 51 and the casing 41, and in which the ends 47 of the degassing capillaries 45 terminate in the circumferential groove. The downstream cap 42 is connected by means of snap locks 43 to the casing 41, the snap locks 43 being formed as clips and latching into catches 52 of the casing 41. In the area of the sealing compound 51, it is advisable, for better sealing, to provide for at least one ring (not shown). The casing 41 has an inlet connection 48.

In the embodiments illustrated in FIGS. 8 and 9, the filter capillaries 34 or 44 may be present in the form of several woven fabrics laminated one on top of the other, the filter capillaries 34 or 44 being present as warp threads in this woven fabric. In the embodiment illustrated in FIG. 8, the degassing capillaries 33 additionally may also be disposed as warp threads in this woven fabric. However, the degassing capillaries may also be woven only with each other as warp threads. In this case it is particularly recommended that a woven hose be used.

If in the embodiment shown in FIG. 9, the snap lock 43 is formed not as a stud but as a circumferential ring, then this circumferential ring, the downstream cap 42, the sealing compound 51, and the casing 41 form a circulating annular duct in which a reduced pressure can be applied in the circumferential ring through an entry fitting not shown.

What is claimed is:

1. A device for separating gas bubbles from liquids, comprising: a casing having a circumferential groove and at least one inlet opening for a liquid to be degassed, at least one outlet opening for degassed liquid, and at least one casing outlet opening for gas in communication with said groove; and a liquid repellent, gas permeable, microporous degassing element disposed at least partially within an area of said casing in which gas bubbles occur, said degassing element comprising at least one degassing capillary having an inner cavity and at least one capillary outlet opening for gas, said inner cavity being closed against entry of liquid and said capillary outlet opening for gas being in communication with said casing outlet opening for gas and thereby in communication with said groove.

2. The device according to claim 1, wherein said degassing capillary is disposed in an axial direction of the casing and wherein at least one end of said capillary serves as said capillary outlet opening for gas.

3. The device according to claim 1, wherein several degassing capillaries are distributed along a periphery of an inner face of the casing.

4. The device according to claim 3, wherein the degassing capillaries are so disposed as to run from one wall portion of said casing to an opposite wall portion of said casing in such a way that the degassing capillaries form with one another a net-type structure which is disposed at least partially perpendicular to the direction of flow of the liquid to be degassed.

5. The device according to claim 2, wherein several said degassing capillaries are disposed parallel to one another and are in the form of a small band.

6. The device according to claim 4, wherein the degassing capillaries comprise at least one of weft and warp threads of a woven fabric.

7. The device according to claim 1, further comprising a wettable, gas-impermeable, microporous filter which subdivides the casing into a first compartment with the inlet opening for liquid and a second compartment with the outlet opening for liquid, said at least one degassing capillary being disposed at least above the filter in a space between the filter and a wall portion of said casing.

8. The device according to claim 7, wherein said filter comprises at least one filter capillary and an inner cavity of said filter capillary at least partially forms said second compartment.

9. The device according to claim 8, wherein said at least one degassing capillary is wound several times loosely around said at least one filter capillary along a length of said at least one filter capillary.

10. The device according to claim 8, wherein a plurality of said filter capillaries is arranged in the form of a bundle, and said at least one degassing capillary is disposed along a circumference of said bundle.

11. The device according to claim 8, wherein said filter capillaries and degassing capillaries are combined as at least one of weft and warp threads in at least one woven fabric.

12. The device according to claim 8, wherein said casing is tubular and the filter capillaries and the degassing capillaries are disposed in said tubular casing in the form of an extended U, all ends of the filter and degassing capillaries being embedded at an embedment point at one end of the casing in a sealing compound in such a way that only said filter capillaries terminate in a central area of the embedment point, and only said degassing capillaries terminate in an outer area of the embedment point; said one end of the casing provided with the sealing compound being shut off by a downstream cap containing said outlet opening for the degassed liquid, said ends of the filter capillaries terminating inside said downstream cap, and said ends of the degassing capillaries terminating outside said downstream cap.

13. The device according to claim 12, wherein said ends of the degassing capillaries are disposed substantially axially parallel to the casing.

14. The device according to claim 12, wherein said circumferential groove is formed between the downstream cap, the sealing compound and the casing.

15. The device according to claim 12, wherein a ring is disposed as a seal between said downstream cap and said sealing compound in an area between the ends of the filter capillaries and the ends of the degassing capillaries.

16. The device according to claim 1, wherein said device is adapted to separate gas bubbles from infusion liquids or human-body liquids to be introduced into a patient's body.

* * * * *